United States Patent [19]

Suto et al.

[11] Patent Number: 5,194,631

[45] Date of Patent: Mar. 16, 1993

[54] PROCESS FOR PRODUCING CARBOXYLIC ACIDS

[75] Inventors: Keiji Suto, Nishinomiya; Koji Nakasa, Osaka; Masaaki Kudo, Kadoma; Moriharu Yamamoto, Kobe, all of Japan

[73] Assignee: Nihon Nohyaku Co., Ltd., Tokyo, Japan

[21] Appl. No.: 378,284

[22] Filed: Jul. 11, 1989

Related U.S. Application Data

[63] Continuation-in-part of Ser. No. 166,544, Mar. 10, 1988, abandoned.

[30] Foreign Application Priority Data

Mar. 14, 1987 [JP] Japan .................................. 62-59686
Feb. 13, 1988 [JP] Japan .................................. 63-31140

[51] Int. Cl.$^5$ .................. C07D 333/38; C07D 307/78; C07D 453/02; C07C 51/10
[52] U.S. Cl. ........................... 549/71; 549/468; 549/484; 546/134; 546/318; 546/122; 562/406
[58] Field of Search ................. 549/71, 468, 484; 562/406; 546/134, 318, 122

[56] References Cited

U.S. PATENT DOCUMENTS 2,565,461 8/1951 Bliss .
3,988,358 10/1976 Heck .
4,034,004 7/1977 Cassar et al. ......................... 562/406

FOREIGN PATENT DOCUMENTS 0086281 8/1983 European Pat. Off. .
0239145 9/1987 European Pat. Off. .

Primary Examiner—Alan Siegel

Attorney, Agent, or Firm—Cushman, Darby & Cushman

[57] ABSTRACT

A process for producing a carboxylic acid which comprises reacting an organic chloride having at least one chloride atom on its ring of a substituted or unsubstituted, aromatic or heterocyclic hydrocarbon with carbon monoxide in the presence of an inorganic base or an organic base and water at a reaction temperature of 150° to 300° C., and preferably 160° to 300° C., by using as catalysts a palladium compound and a phosphine compound represented by the general formula (III):

$$(R)_2P-X-P(R)_2 \qquad (III)$$

wherein R is an alkyl group or a substituted or unsubstituted phenyl group, and X is an alkylene group having 1 to 6 carbon atoms,

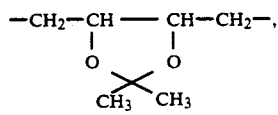

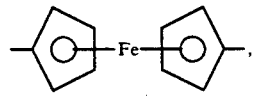

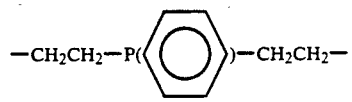

or a binaphthyl group.

12 Claims, No Drawings

PROCESS FOR PRODUCING CARBOXYLIC ACIDS

This is a continuation-in-part of application Ser. No. 07/166,544, filed Mar. 10, 1988, now abandoned.

FIELD OF THE INVENTION AND RELATED ART STATEMENT

This invention relates to a process for producing an aromatic or heterocyclic carboxylic acid and more particularly it relates to a process for producing a carboxylic acid represented by the general formula (I):

$$R^1\text{-COOH} \qquad (I)$$

(wherein $R^1$ is a substituted or unsubstituted, aromatic or heterocyclic hydrocarbon group), which comprises reacting an organic chloride represented by the general formula (II):

$$R^1\text{-Cl} \qquad (II)$$

(wherein $R^1$ has the same meaning as defined above) with carbon monoxide at a reaction temperature of 150° to 300° C., and preferably 160° to 300° C., in the presence of a carbonylation catalyst composed of a palladium compound and a phosphine compound represented by the general formula (III):

$$(R)_2P\text{—}X\text{—}P(R)_2 \qquad (III)$$

(wherein R is an alkyl group or a substituted or unsubstituted phenyl group, and X is an alkylene group having 1 to 6 carbon atoms,

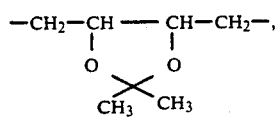

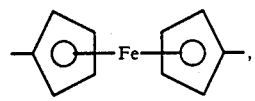

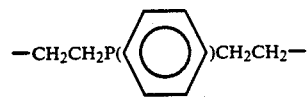

or a binaphthyl group), and an inorganic base or an organic base/water.

The carboxylic acids of the general formula (I) obtained by this invention are useful not only as medicines and agricultural chemicals but also as various industrial materials, and the present invention provides a novel process for producing these carboxylic acids.

RELATED ART

As a conventional process for producing a carboxylic acid, there is suggested in U.S. Patent 3988358 a process in which carboxylic acid is produced by reacting an aromatic halide with carbon monoxide and water in the presence of a palladium/phosphine catalyst. However, this process is not exemplified by Working Examples in U.S. Pat. No. 3,988,358.

In J.O.C. 1981, 46, 4614–4617, a process for producing a carboxylic acid from an aryl halide is described, but although the desired carboxylic acid can be obtained from a bromide, it cannot be obtained from a chloride because no reaction proceeds.

Jap. Pat. Appln. Kokai (Laid-Open) No. 61-233648 discloses a process in which a poly(arylcarboxylic acid) is produced under irradiation with light by using cobalt carbonyl as a catalyst. However, since this process is practised under irradiation with light, it requires facilities for the irradiation and its industrialization entailes great cost. Moreover, this process uses cobalt carbonyl and hence is disadvantageous also from the viewpoint of toxicity. As a process in which calbonylation of an aromatic chloride is carried out, Jap. Pat. Appln. Kokai (Laid-Open) No. 61-293950 discloses a process for producing a carboxylic acid using a chloro- or bromo-allenecarbonylchromium compound, but this process is disadvantageous in that a tricarbonylchromium complex as reaction substrate should be produced.

As described above, the reactions of aromatic iodides or bromides with carbon monoxide are known, but there is not known any process in which an aromatic or heterocyclic carboxylic acid is synthesized by the reaction of an aromatic or heterocyclic chloride with carbon monoxide.

SUMMARY OF THE INVENTION

In consideration of such conditions, the present inventors earnestly investigated the reactions of aromatic or heterocyclic chlorides with carbon monoxide and consequently established a process for producing an aromatic or heterocyclic carboxylic acid in a high yield, whereby the present invention has been accomplished.

The process for producing a carboxylic acid of this invention can be schematically represented, for example, as follows:

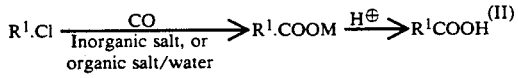

wherein $R^1$ has the same meaning as defined above, and M is a base residue.

That is to say, an organic chloride of the general formula (II) is reacted with carbon monoxide at a reaction temperature of 150° to 300° C., and preferably 160° to 300° C., in the presence or absence of a solvent in the presence of a carbonylation catalyst composed of a palladium compound and a phosphine compound of the general formula (III):

$$(R)_2P\text{—}X\text{—}P(R)_2 \qquad (III)$$

(wherein R is an alkyl group or a substituted or unsubstituted phenyl group, and X is an alkylene group having 1 to 6 carbon atoms,

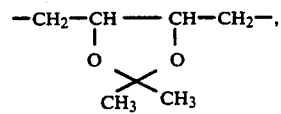

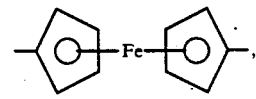

or a binaphthyl group), and an inorganic base or an organic base/water, whereby a desired carboxylic acid of the general formula (I) can be obtained.

DETAILED DESCRIPTION OF PREFERRED EMBODIMENTS

When an inorganic salt is used in the reaction of this invention, addition of water is not necessary because water generated by the reaction is present in the reaction system, but when an organic base is used therein, use of water is essential and the using amount is equimolar with or in excess of the organic chloride of the general formula (II).

The organic chloride of the general formula (II) in this invention may be any one so long as it has at least one chlorine atom on its ring of a substituted or unsubstituted, aromatic or heterocyclic hydrocarbon. It includes also fused ring hydrocarbons and fused heterocyclic ring hydrocarbons. Typical examples of said organic chloride includes, for example, aromatic organic chlorides such as chlorobenzene, dichlorobenzene, trichlorobenzene, tetrachlorobenzene, pentachlorobenzene, hexachlorobenzene, chlorofluorobenzene, chlorodifluorobenzene, chlorotrifluorobenzene, chlorotetrafluorobenzene, chloropentafluorobenzene, trifluoromethylchlorobenzene, chlorotoluene, dichlorotoluene, trichlorotoluene, chloroxylene, dichloroxylene, trichloroxylene, chlorophenol, chloroanisole, chloronitrobenzene, dichloronitrobenzene, chlorocyanobenzene, chlorophenylacetic acid esters, N-acetylchloroaniline, chloroacetophenone, chlorobenzophenone, chloromethylthiobenzene, chlorobenzoic acid esters, chlorodiphenyl ether, dichlorodiphenyl ether, dichlorobenzophenone, dichlorodiphenyl sulfone, dichlorodiphenylmethane, dichlorodiphenyl, chloronaphthalene, chloromethylnaphthalene, chloroanthraquinone, and the like; and heterocyclic organic chlorides such as chlorothiophene, chlorofuran, chloroindole, chloropyridine, dichloropyridine, chloropicoline, chloroquinoline, chloroquinoxaline, dichloroquinoxaline, and the like. The organic chloride may be used in a predetermined amount only as a reactant, or it may be added in excess and used both as a reactant and a solvent.

The palladium compound as carbonylation catalyst in this invention is used in combination with a phosphine compound. The palladium compound includes, for example, metallic palladium, palladium carbon, palladium alumina, palladium chloride, pallaidum bromide, palladium acetate, dichlorobiscyanophenylpalladium, dichlorobistriphenylphosphine palladium, tetrakistriphenylphosphine palladium, etc. The phosphine compound of the general formula (III) includes, for example, bis(dialkylphosphino)alkanes such as 1,1-bis(dimethylphosphino)methane, 1,1-bis(diethylphosphino)methane, 1,2-bis(dimethylphosphino)ethane, 1,2-bis(diethylphosphino)ethane, 1,3-bis(dimethylphosphino)propane, 1,4-bis(dimethylphosphino)butane, and the like, bis(diphenylphosphino)alkanes such as 1,1-bis(diphenylphosphino)methane, 1,2-bis(diphenylphosphino)ethane, 1,3-bis(diphenylphosphino)propane, 1,4-bis(diphenylphosphino)butane, 1,5-bis(diphenylphosphino)pentane, 1,6-bis(diphenylphosphino)hexane, 2,3-O-isopropylidene-2,3-dihydroxy-1,4-bisdiphenylphosphinobutane, and the like, bisdiphenylphosphinoferrocene, bisdiphenylphosphinobinaphthyl, 1,2-bis(diphenylphosphino)benzene, 1,1-bis(dibenzophosphoryl)methane, 1,2-bis(dibenzophosphoryl)ethane, 1,3-bis(dibenzophosphoryl)propane, 1,4-bis(dibenzophosphoryl)butane, 1,5-bis(dibenzophosphoryl)pentane, etc.

The adding amount of the phosphine compound is 0.01 to 10,000 moles, preferably 0.1 to 100 moles per mole of the palladium compound.

In this invention, the palladium compound and the phosphine compound of the general formula (III) are used in combination and may be used in the reaction system either individually or in the form of a previously prepared complex.

Although not critical, the total amount of the palladium compound and the phosphine compound added to the reaction system is 0.0001 to 0.5 mole, preferably 0.001 to 0.1 mole per mole of the organic chloride of the general formula (II).

The inorganic base used in this invention includes sodium carbonate, potassium carbonate, sodium hydroxide, potassium hydroxide, etc. The organic base used therein includes triethylamine, tributylamine, diisopropylethylamine, triisooctylamine, pyridine, N-methylpyrrolidine, N-methylmorpholine, N-ethylmorpholine, etc.

Although the base is used preferably in an amount required for neutralization of hydrogen chloride generated, the using amount may, of course, be smaller or larger than this amount.

When an organic base is used, use of water is essential and the using amount of water is 0.1 to 100 moles per mole of the organic chloride.

The reaction in this invention can be carried out in the presence or absence of a solvent, and any solvent can be used so long as it does not inhibit the reaction seriously. As such a solvent, there may be exemplified, for example, organic solvents such as hexane, benzene, ether, tetrahydrofuran, acetonitrile, dimethylformamide, hexamethylphosphotriamide, acetone, etc.

The reaction in this invention is carried out at atmospheric pressure or under pressure. The pressure of carbon monoxide is properly selected in the range of 1 to 200 atmospheres, preferably 1 to 50 atmospheres.

The reaction temperature in this invention is 150° to 300° C., preferably 150° to 250° C., and most preferably 160° to 250° C.

As a reactor used in this invention, a conventional one may be used. When the reaction is carried out under pressure, any reactor may be used so long as it can withstand the reaction pressure, and usually a reactor made of metal or glass is used.

Although varied depending on the amounts of the reactions and the reaction temperature, the reaction time is selected in the range of several minutes to 48 hours.

In this invention, when the organic chloride of the general formula (II) is an organic polychlorinated compound, the chlorine atoms on the ring can be selectively made into acid in turn.

A desired compound can be obtained by treating the reaction mixture by a conventional method after completion of the reaction.

Examples of this invention are described below but are not by way of limitation but by way of illustration.

EXAMPLE 1

Production of benzoic acid

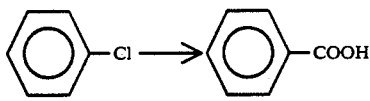

In an autoclave made of metal were placed 11.2 g of chlorobenzene, 17.5 mg of palladium chloride, 427 mg of bisdiphenylphosphinobutane and 3.1 g of potassium carbonate. The air in the autoclave was replaced with carbon monoxide introduced thereinto in several times, after which carbon monoxide was further introduced to its pressure therein to 50 kg/cm$^2$. The reaction was carried out with stirring for 3 hours on a salt bath at a bath temperature of 210° C. After completion of the reaction, the reaction mixture was cooled to room temperature and water was added. The aqueous layer was separated, after which acid was added thereto and the deposited crystals were collected by filtration and dried to obtain 0.97 g of the desired compound benzoic acid.

Melting point 122°-123° C.

EXAMPLE 2

Production of ortho-chlorobenzoic acid

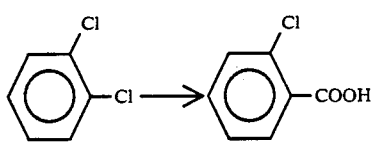

The procedure of Example 1 was repeated, except that 14.7 g of ortho-dichlorobenzene was used in place of 11.2 g of chlorobenzene. Thus, 0.77 g of the desired compound ortho-chlorobenzoic acid was obtained.

Melting point 138°-140° C.

EXAMPLE 3

Production of ortho-methylbenzoic acid

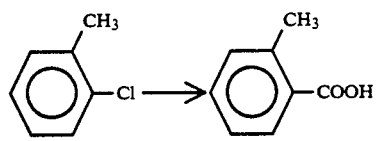

The procedure of Example 1 was repeated, except that 12.6 g of ortho-chlorotoluene was used in place of 11.2 g of chlorobenzene. Thus, 2.35 g of the desired compound ortho-methylbenzoic acid was obtained.

Melting point 103°-105° C.

EXAMPLE 4

Production of para-chlorobenzoic acid

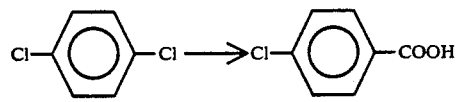

In an autoclave made of metal were placed 2.78 g of para-dichlorobenzene, 17.5 mg of palladium chloride, 427 mg of bisdiphenylphosphinobutane, 3.1 g of potassium carbontae and 30 ml of acetonitrile. The air in the autoclave was replaced with carbon monoxide introduced thereinto in several times, after which carbon monoxide was further introduced to adjust its pressure therein to 50 kg/cm$^2$. The reaction was carried out with stirring for 3 hours on a salt bath at a bath temperature of 250° C. After completion of the reaction, the reaction mixture was cooled to room temperature and water was added. The aqueous layer was separated and then acid was added thereto, followed by extraction from the aqueous layer with ether. The ether layer was dried and then concentrated to obtain 0.6 g of para-chlorobenzoic acid.

Melting point 239°-241° C.

EXAMPLE 5

Production of 2,3-dichlorobenzoic acid

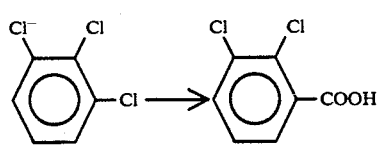

The procedure of Example 4 was repeated, except that 18.1 g of 1,2,3-trichlorobenzene was used in place of 2.78 g of para-dichlorobenzene. Thus, 1.43 g of the desired compound 2,3-dichlorobenzoic acid was obtained.

Melting point 167°-169° C.

EXAMPLE 6

Production of ortho-trifluoromethylbenzoic acid

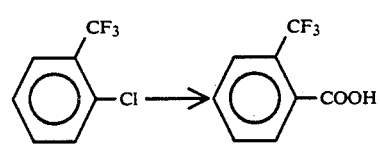

In an autoclave made of metal were placed 18 g of ortho-chlorobenzotrifluoride, 3.5 mg of palladium chloride, 170 mg of bisdiphenylphosphinobutane and 3.1 g of potassium carbonate. The air in the autoclave was replaced with carbon monoxide introduced thereinto in several times, after which carbon monoxide was further introduced to adjust its pressure therein to 30 kg/cm$^2$. The reaction was carried out with stirring on a salt bath at a bath temperature of 240° C. After completion of the reaction, the reaction mixture was cooled to room temperature and water was added. The aqueous layer was separated and then acid was added thereto, followed by extraction from the aqueous layer. The ether layer was dried and then concentrated to obtain 3.9 g of ortho-trifluoromethylbenzoic acid.

Melting point 109°-113° C.

EXAMPLE 7

Production of ortho-trifluorobenzoic acid

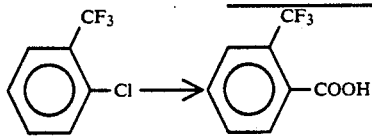

In an autoclave made of metal were placed 18 g of ortho-chlorobenzotrifluoride, 3.5 mg of palladium chloride, 170 mg of bisdiphenylphosphinobutane and 23 g of sodium carbonate. The air in the autoclave was replaced with carbon monoxide introduced thereinto in several times, after which carbon monoxide was further introduced to adjust its pressure therein to 30 kg/cm$^2$. The reaction was carried out with stirring for 5 hours on a salt bath at a bath temperature of 210° C. After completion of the reaction, the reaction mixture was cooled to room temperature and water was added. The aqueous layer was separated and then acid was added thereto, followed by extraction from the aqueous layer with ether. The ether layer was dried and then concentrated to obtain 2.8 g of ortho-trifluoromethylbenzoic acid.

EXAMPLE 8

Production of meta-methylbenzoic acid

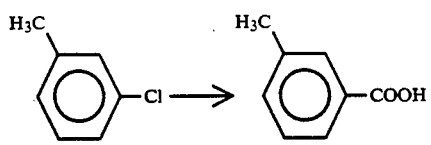

In an autoclave made of metal were placed 2.53 g of meta-chlorotoluene, 35.5 mg of palladium chloride, 426 mg of bisdiphenylphosphinobutane and 3.04 g of potassium carbonate. The air in the autoclave was replaced with carbon monoxide introduced thereinto in several times, after which carbon monoxide was further introduced to adjust its pressure therein to 50 kg/cm$^2$. The reaction was carried out with stirring for 3 hours on a salt bath at a bath temperature of 210° C. After completion of the reaction, the reaction mixture was cooled to room temperature and water was added. The aqueous layer was separated, after which acid was added thereto and the deposited crystals were collected by filtration and dried. Thus, 1.10 g of the desired compound meta-methylbenzoic acid was obtained.

Melting point 107°–110° C.

EXAMPLE 9

The procedure of Example 8 was repeated, except that each chloride and each base listed in Table 1 were used in place of the chloride and the base, respectively, used in Example 8.

TABLE 1

| Example | Chloride | | Base | | Acid | |
|---|---|---|---|---|---|---|
| 9-1 | p-Chlorotoluene | 1.27 g | Potassium carbonate | 1.52 g | p-Methylbenzoic acid | 0.67 g |
| 9-2 | 1,2-Dichlorobenzene | 2.92 g | Sodium carbonate | 2.33 g | o-Chlorobenzoic acid | 2.19 g |
| 9-3 | 1,3-Dichlorobenzene | 2.92 g | Sodium carbonate | 2.33 g | m-Chlorobenzoic acid | 0.78 g |
| 9-4 | 1,2,4,5-Tetrachlorobenzene | 21.5 g | Sodium carbonate | 11.66 g | 2,4,5-Trichlorobenzoic acid | 1.38 g |
| 9-5 | 2,5-Dichloroparaxylene | 3.50 g | Potassium carbonate | 3.04 g | 4-Chloro-2,5-dimethylbenzoic acid | 2.16 g |
| 9-6 | 4-Chlorocyanobenzene | 2.75 g | Sodium carbonate | 2.75 g | p-Cyanobenzoic acid | 1.78 g |

EXAMPLE 10

Production of para-methoxybenzoic acid

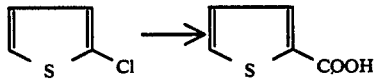

In an autoclave made of metal were placed 2.85 g of para-methoxychlorobenzene, 35.5 mg of palladium chloride, 426 mg of bisdiphenylphosphinobutane and 30 mg of benzene. The air in the autoclave was replaced with carbon monoxide introduced thereinto in several times, after which carbon monoxide was further introduced to adjust its pressure therein to 40 kg/cm$^2$. The reaction was carried out with stirring for 3 hours on a salt bath at a bath temperature of 220° C. After completion of the reaction, the reaction mixture was cooled to room temperature and water was added. The benzene layer and the aqueous layer was separated from each other, after which acid was added to the aqueous layer, and the deposited crystals were collected by filtration and dried to obtain 1.57 g of the desired compound.

Melting point 183.5°–184° C.

EXAMPLE 11

Production of thiophene-2-carboxylic acid

In an autoclave made of metal were placed 7.1 g of 2-chlorothiophene, 17.5 mg of palladium chloride, 426 mg of bisdiphenylphosphinobutane, 3.0 g of potassium carbonate, and 7.8 g of benzene. The air in the autoclave was replaced with carbon monoxide introduced in several times, after which carbon monoxide was further introduced to adjust its pressure therein to 30 kg/cm$^2$. The reaction was carried out with stirring for 3 hours on a salt bath at a bath temperature of 225° C. After completion of the reaction, the reaction mixture was cooled to room temperature and water was added. The benzene layer and the aqueous layer were separated from each other, after which acid was added to the aqueous layer and the deposited crystals were collected by filtration and dried to obtain 0.35 g of the desired compound thiophene-2-carboxylic acid.

Melting point 127°–134° C.

EXAMPLE 12

Production of para-trifluoromethylbenzoic acid

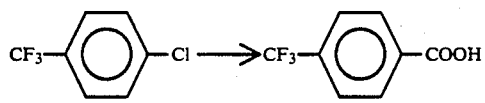

In an autoclave made of glass were placed 180.6 g of parachlorobenzotrifluoride, 0.64 g of 5% palladium-carbon, 4.3 g of 1,4-bisdiphenylphosphinobutane and 21.2 g of sodium carbonate. The air in the autoclave was replaced with carbon monoxide introduced thereinto several times, after which carbon monoxide was further introduced to adjust its pressure therein to 10 kg/cm². The reaction was carried out with stirring for 8 hours at 180° C. After completion of the reaction, the reaction mixture was cooled to room temperature and water was added. The aqueous layer was separated and then acid was added thereto, followed by extraction from the aqueous layer with ether. The ether layer was dried and then concentrated to obtain 101 g of paratrifluoromethylbenzoic acid.

Melting point 218°–220° C.

What is claimed is:

1. A process for producing a carboxylic acid which comprises reacting an organic chloride having at least one chlorine atom on its ring of a substituted or unsubstituted, aromatic or heterocyclic hydrocarbon with carbon monoxide in the presence of an inorganic base at a reaction temperature of 160° to 300° C. by using as catalysts a palladium compound and a phosphine compound represented by the general formula (III):

wherein R is an alkyl group or a substituted or unsubstituted phenyl group, and X is an alkylene group having 1 to 6 carbon atoms,

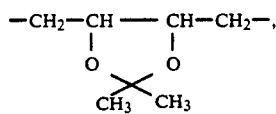

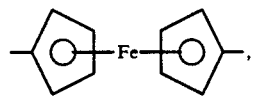

or a binaphthyl group.

2. A process for producing a carboxylic acid according to claim 1, wherein the palladium compound is metallic palladium, metallic palladium supported on a solid, or a zerovalent, divalent or tetravalent palladium complex.

3. A process for producing a carboxylic acid according to claim 2, wherein the palladium compound is palladium carbon, palladium chloride or palladium acetate.

4. A process for producing a carboxylic acid according to claim 3, wherein the phosphine compound is a bis(diphenylphosphino)alkane.

5. A process for producing a carboxylic acid according to claim 4, wherein the base is sodium carbonate or potassium carbonate.

6. A process for producing a carboxylic acid according to claim 5, wherein the pressure of carbon monoxide is 1 to 200 atmospheres.

7. A process for producing a carboxylic acid which comprises reacting an organic chloride having at least one chlorine atom on its ring of a substituted or unsubstituted, aromatic or heterocyclic hydrocarbon with carbon monoxide and water in the presence of an organic base at a reaction temperature of 160° to 300° C. by using as catalysts a palladium compound and a phosphine compound represented by the general formula (III):

wherein R is an alkyl group or a substituted or unsubstituted phenyl group, and X is an alkylene group having 1 to 6 carbon atoms,

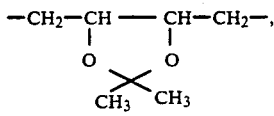

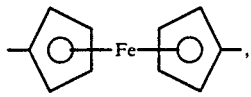

or a binaphthyl group.

8. A process for producing a carboxylic acid according to claim 7, wherein the palladium compound is a metallic palladium, metallic palladium supported on a solid, or a zerovalent, divalent or tetravelent palladium complex.

9. A process for producing a carboxylic acid according to claim 8, wherein the palladium compound is palladium carbon, palladium chloride or palladium acetate.

10. A process for producing a carboxylic acid according to claim 8, wherein the phosphine compound is a bis(diphenylphosphino)alkane.

11. A process for producing a carboxylic acid according to claim 10, wherein the base is tributylamine or N-ethylmorpholine.

12. A process for producing a carboxylic acid according to claim 11, wherein the pressure of carbon monoxide is 1 to 200 atmospheres.

* * * * *